United States Patent [19]

Kohsaka et al.

[11] Patent Number: 4,726,216

[45] Date of Patent: Feb. 23, 1988

[54] SENSITIVITY-CALIBRATION CIRCUIT FOR AN HC ANALYZER

[75] Inventors: Hiroji Kohsaka; Nobutaka Kihara; Yoshiyuki Nakajima; Kennosuke Kojima, all of Minami, Japan

[73] Assignee: Horiba, Ltd., Kyoto, Japan

[21] Appl. No.: 906,011

[22] Filed: Sep. 11, 1986

[30] Foreign Application Priority Data

Nov. 27, 1985 [JP] Japan .............. 60-183440[U]

[51] Int. Cl.$^4$ .................................. G01N 27/00
[52] U.S. Cl. ........................................ 73/1 G
[58] Field of Search ................... 73/1 G, 23, 1 R

[56] References Cited

U.S. PATENT DOCUMENTS 3,975,947  8/1976  Kruishoop ............... 73/1 G
4,032,856  6/1977  Goldner .................. 73/23
4,348,732  9/1982  Kreft ........................ 73/23
4,447,780  5/1984  Youmans et al. ........ 73/23
4,482,251 11/1984  Saylor ..................... 356/418
4,494,399  1/1985  Youngman ............... 73/1 G Primary Examiner—Stewart J. Levy
Assistant Examiner—Robert R. Raevis
Attorney, Agent, or Firm—Wenderoth, Lind & Ponack

[57] ABSTRACT

A sensitivity-calibration circuit for an HC analyzer includes a scale factor adjuster for setting a scale factor in the analyzer for determining an n-hexane reduced gas concentration value of propane gas used during sensitivity-calibration of the analyzer and a sensitivity adjuster for adjusting the sensitivity of the analyzer and a switching means for switching the circuit between a first calibration state and a second measurement state.

4 Claims, 2 Drawing Figures

SENSITIVITY-CALIBRATION CIRCUIT FOR AN HC ANALYZER

BACKGROUND OF THE INVENTION

1. Field of the Invention

The present invention relates to a sensitivity-calibration circuit for an HC analyzer for detecting the concentration of "HC gases" such as methane ($CH_4$) and ethane ($C_2H_6$) as an n-hexane reduced gas-concentration value.

2. Description of the Prior Art

Although the sensitivity-calibration in a HC analyzer of this type should be always carried out using the standard n-hexane gas (having a known concentration) in a nature of things, in fact it is carried out using substitute gases since n-hexane gas has an unstable property of very easily being liquefied.

That is to say, the sensitivity-calibration has been carried out in the following manner:

At first, in the initial adjustment of a HC analyzer, at first an appointed sensitivity-calibration has been carried out by the use of a standard n-hexane gas having a known concentration and then a standard propane gas also having a known concentration $C_p$ has been passed through the HC analyzer to measure the concentration thereof. A scale factor $P_c$ inherent to said HC analyzer is determined from the measured value (corresponding to the n-hexane reduced gas-concentration $C_N$ of the standard propane gas-concentration $C_p$) by the HC analyzer. The scale factor $P_c$ (for example, the scale factor for an n-hexane gas-concentration: 0.521) is then recorded on a display label and is affixed to the HC analyzer.

Now, said scale factor $P_c$ is determined by the calculation based on the following equation [I]:

$$P_c = C_N / C_p \quad [I]$$

wherein $C_N$: a measured value by the HC analyzer (a n-hexane reduced gas-concentration value of a standard propane gas)

$C_p$: a standard propane gas-concentration.

And, in the usual calibration when the analyzer requires recalibration after the initial adjustment, at first the n-hexane reduced gas concentration value $C_N$ of standard propane gas is determined in accordance with the following equation ([II] which is a modification of said equation [I]) on the basis of the known concentration $C_P$ of standard propane gas to be used (this is recorded on a display label affixed to a gas cylinder in a manner of, for example, concentration: 1,862 ppm [$C_3H_8$]) and the scale factor $P_c$ inherent to the HC analyzer and previously recorded on the display label is also affixed to the HC analyzer in the above described manner.

N-hexane reduced gas-concentration value $C_N$

= the concentration $C_p$ of standard propane gas $\times$ the scale factor $P_c$ ($= 1,862 \times 0.521 =$ about 970)     [II]

Then, the standard propane gas is passed through the HC analyzer and the sensitivity-calibration circuit in the HC analyzer is adjusted so that an output of the HC analyzer may indicate the n-hexane reduced gas-concentration value $C_N$ (for example 970 ppm) determined in the above described manner.

However, with the above described conventional means, as is obvious from the technique described above, each HC analyzer has a scale factor $P_c$ which is inherent and different due to minor differences in their optical systems. Moreover, since the scale factor $P_c$ is usually a complex value, such as 0.521, consisting of many digits, a disadvantage has occurred in that complicated calculations of multiple digit numbers on the basis of the above described equations must be carried out for every calibration after the initial adjustment.

SUMMARY OF THE INVENTION

It is an object of the present invention to provide a sensitivity-calibration circuit for an HC analyzer which is capable of easily achieving the setting of a scale factor $P_c$ in the HC analyzer at a simple numerical value, which can be easily calculated, so that the calculation of determining an n-hexane reduced gas-concentration value $C_N$ of a standard propane gas used for the calibration may be easily carried out.

In order to achieve the above described object, a sensitivity-calibration circuit for an HC analyzer according to the present invention is characterized by the fact that a scale factor-adjusting means is provided for setting a scale factor $P_c$ in said analyzer for determining an n-hexane reduced gas-concentration value $C_N$ of a propane gas used in the sensitivity-calibration of the analyzer.

The effects exhibited by the above described characteristical construction are as follows:

In the sensitivity-calibration circuit in the HC analyzer according to the present invention, since the factor-adjusting means, which is capable of setting a scale factor $P_c$ for determining an n-hexane reduced gas-concentration value $C_N$ of a propane gas used in the sensitivity-calibration, (for example, a potentiometer), is provided, during the initial adjustment of the HC analyzer, said scale factor $P_c$ can be easily set at a simple numerical value (so to speak, a round number), such as 0.500 ($=\frac{1}{2}$), which can be easily calculated, by operating said scale factor-adjusting means, whereby the calculation of $C_N$ on the basis of said equation [II]: n-hexane reduced gas-concentration value $C_N =$ a concentration $C_p$ of standard propane gas $\times$ a scale factor $P_c$ can be achieved easily with significantly less calculation (only one multiplication or division) in comparison with the conventional sensitivity-calibration circuit, for example, $C_N = 1,862 \times 0.5 = 931$ or $1,862 \, 2 = 931$.

In addition, if the present invention is applied to HC analyzers of the same type, a scale factor $P_c$ of an optional specified numerical value (for example 0.500), which can be easily calculated in the same manner as described above, can be easily set in common for all of those HC analyzers. In such a case, the calibration can be remarkably simply and speedily carried out without requiring any calculation at all by recording not only the concentration $C_p$ but also a product of the concentration $C_p$ of the standard propane gas and the common scale factor $P_c$ for all of said HC analyzers, in short, an n-hexane reduced gas-concentration value $C_N$ of the standard propane gas itself, on a display label of a cylinder of standard propane gas used in the sensitivity-calibration after the initial adjustment of the HC analyzer. In the above described explanation an example of setting the scale factor $P_c$ at a value not equal to 1.00, which is the most simple numerical value, but a specified numerical value of 0.500 was shown. Its reason was that "confused sense" of a user (an engineer) could be prevented by setting the scale factor $P_c$ at round numbers which are not greatly different from a real scale factor $P_c$ (for example 0.521). It goes without saying that it is necessary for merely simplifying (in short making unnecessary) the calculation only to set the scale factor $P_c$ at 1.00 which is the most simple numerical value.

BRIEF DESCRIPTION OF THE DRAWINGS

The preferred embodiments of a sensitivity-calibration circuit for an HC analyzer according to the present invention are shown in the accompanying drawings, in which.

DESCRIPTION OF THE PREFERRED EMBODIMENTS

The preferred embodiments of a sensitivity-calibration circuit for an HC analyzer according to the present invention is described below with reference to the drawings.

Figure 1:
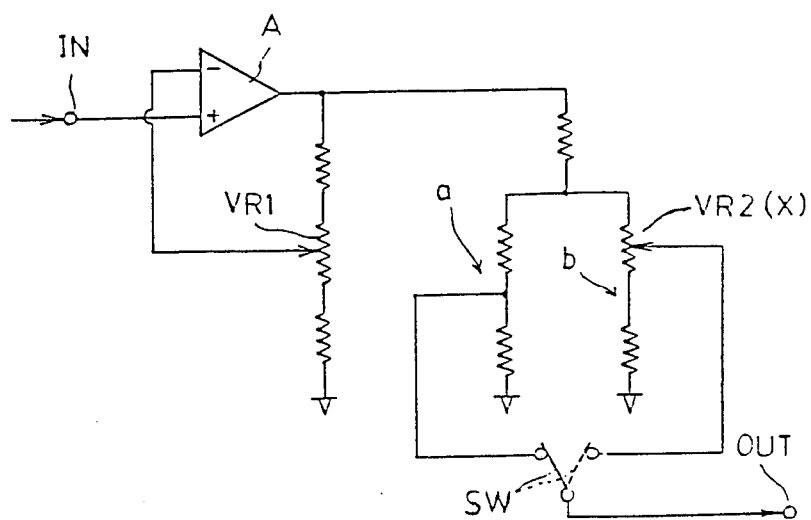
FIG. 1 is a block diagram showing a circuit of one preferred embodiment of the present invention.

Referring now to FIG. 1, showing a preferred embodiment, A designates an operational amplifier for amplifying a concentration-detecting signal voltage supplied from a HC analyzer (not shown) through an input terminal IN; VR1 designates a sensitivity-calibration potentiometer for adjusting the sensitivity by controlling an amplification factor of the operational amplifier A, and SW designates a switch which can be switched over to one state, in which an output signal is fed from the operational amplifier A to an output terminal OUT through a voltage divider "a" of a measurement side (shown by a solid line), and another state, in which the output signal is fed from the operational amplifier A to the output terminal OUT through a voltage divider "b" of a calibration side (shown by a dotted line).

The voltage divider "b" of the calibration side is provided with a trimmer potentiometer VR2 composing a scale factor-adjusting means X capable of setting a scale factor $P_c$ in the analyzer for determining an n-hexane reduced gas-concentration value $C_N$ of a propane gas used in the sensitivity-calibration of the HC analyzer at an optional value in the middle thereof.

The sensitivity-calibration of the HC analyzer constructed in the above described manner is carried out as follows:

At first, in the initial adjustment of the HC analyzer, an appointed sensitivity-calibration is carried out by switching over the switch SW to the measurement side, and passing a standard n-hexane gas having a known concentration through the HC analyzer, and adjusting the sensitivity-calibration potentiometer VR1 under such a condition so that an output signal corresponding to the known concentration can be obtained from the output terminal OUT.

Subsequently, the switch SW is switched over to the calibration side and a standard propane gas also having a known concentration $C_p$ (for example 1,862 ppm) is passed through the HC analyzer. If the scale factor $P_c$ for determining the n-hexane reduced gas-concentration value $C_N$ of the propane gas for the HC analyzer including the sensitivity-calibration circuit as a whole is set at an optional specified simple numerical value (for example $0.500 = \frac{1}{2}$), the trimmer potentiometer VR2, used as the scale factor-adjusting means X, may be adjusted so that an output signal is obtained from the output terminal OUT which is in correspondence with the n-hexane reduced gas-concentration value $C_N$ (=931 ppm) determined on the basis of the above described following equation:

N-hexane reduced gas-concentration value $C_N$

= a concentration $C_p$ of standard propane gas

× a scale factor $P_c$     [II]

in short, in a manner of $1{,}862 \times C_p \times 0.5/C_p = 931$ (ppm) and then, the setting of the trimmer potentiometer VR2 is locked so as to be fixed. In the equation [III], $P_c$ is a scale factor inherent to the HC analyzer; $0.5/C_p$ is a scale factor adjusted by VR2.

Thus, since the scale factor $P_c$ in the HC analyzer is set at an optional specified simple numerical value $(0.500 = \frac{1}{2})$ by which the calculation of $C_N$ can be easily carried out, in the subsequent usual calibration, the calculation on the basis of the above described equation:

N-hexane reduced gas-concentration value $C_N$

= a concentration $C_p$ of standard propane gas

× a scale factor $P_c$ can be easily carried out by the use of an optional specified numerical value $(0.500 = \frac{1}{2})$, thereby through an easy calculation of only a few figures (only one multiplication or division) making the calculation easy.

Figure 2:
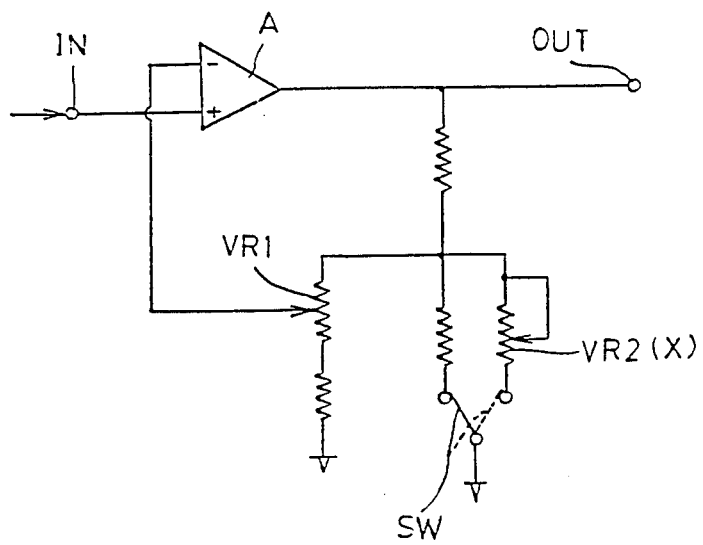
FIG. 2 is a block diagram showing a circuit of another preferred embodiment of the present invention.

In another preferred embodiment as shown in FIG. 2, the amplification factor of the operational amplifier A is varied by switching over the switch SW to the measurement side and calibration sides.

Also, with a sensitivity-calibration circuit in a HC analyzer constructed in such a manner, it goes without saying that an effect, which is fundamentally similar to that in the above described circuit, can be exhibited. Besides, an advantage occurs also in that a low impedance output can be obtained.

What is claimed is:

1. A sensitivity-calibration circuit for an HC analyzer used for detecting the concentration of "HC gases" as an n-hexane reduced gas concentration, said circuit connected to an output of the HC analyzer and comprising: a scale factor-adjusting means for setting a scale factor of the HC analyzer and for determining an n-hexane reduced gas-concentration value of propane gas used during sensitivity-calibration of the HC analyzer, said scale factor-adjusting means being coupled to a sensitivity adjusting means for adjusting the sensitivity of the HC analyzer and to a switching means for switching said sensitivity-calibration circuit between a first calibration state and a second measurement state.

2. A sensitivity-calibration circuit for an HC analyzer as set forth in claim 1, where said scale factor-adjusting means is connected to an output of an operational amplifier whose amplification factor is adjusted by said sensitivity adjusting means which comprises a sensitivity-calibration potentiometer.

3. A sensitivity-calibration circuit for an HC analyzer comprising:

an amplifier having its input connected to an output of the HC analyzer and having an output and including a sensitivity adjusting means for adjusting the gain of said amplifier;

a fixed voltage divider and a variable voltage divider including a scale factor adjusting means, said fixed voltage divider and said variable voltage divider being connected in parallel to said output of said amplifier;

a switching means having an output and first and second inputs, said first input connected to an output of said fixed voltage divider and said second input connected to an output of said variable voltage divider and said output of said switching means comprising an output of said sensitivity-calibration circuit, said switching means connecting its output to its first input when in a first measurement state and connecting its output to its second input in a second calibration state.

4. A sensitivity-calibration circuit for an HC analyzer comprising:

an amplifier having an electrical input connected to an electrical output of the HC analyzer and having an electrical output comprising an output of said sensitivity-calibration circuit;

a sensitivity adjusting means connected to said amplifier for adjusting the gain of said amplifier;

a fixed resistor and a variable resistor coupled to said input of said amplifier, said variable resistor comprising a scale factor adjusting means;

a switch means having first and second inputs and a grounded output, said first and second inputs being respectively connected to said fixed and variable resistors such that said switch means connects said fixed resistor to ground when in a first measurement state and connects said variable resistor to ground when in a second calibration state.

* * * * *